United States Patent [19]

Estep

[11] 4,432,750
[45] Feb. 21, 1984

[54] ADDITIVE STEROL SOLUTION AND METHOD FOR PRESERVING NORMAL RED CELL MORPHOLOGY IN WHOLE BLOOD DURING STORAGE

[75] Inventor: Timothy N. Estep, Lindenhurst, Ill.

[73] Assignee: Baxter Travenol Laboratories, Inc., Deerfield, Ill.

[21] Appl. No.: 326,772

[22] Filed: Dec. 2, 1981

[51] Int. Cl.$^3$ .................... A61M 1/03; A61K 35/14; A01N 1/00
[52] U.S. Cl. ........................................ 604/4; 604/403; 604/262; 424/101; 435/2
[58] Field of Search ............................ 424/101; 435/2

[56] References Cited

U.S. PATENT DOCUMENTS 4,222,379  9/1980  Smith.
4,286,597  9/1981  Gajewski et al.
4,300,559  11/1981 Gajewski et al.
4,301,800  11/1982 Collins.
4,326,025  4/1982  Buckles et al.

OTHER PUBLICATIONS

Ponder, *Hemolysis and Related Phenomena*, Grune and Stratton, New York, 1948, pp. 263–287.
Cooper et al., "Modification of Red Cell Membrane Structure by Cholesterol-Rich Lipid Dispersions", The *Journal of Clinical Investigation*, vol. 55, Jan. 1975, pp. 115–126.
DeVenuto et al., "Distribution of Progesterone and Its Affect on Human Blood During Storage", *Transfusion*, Mar.–Apr. 1976, pp. 107–112.
Little and Rumsby, *Scand. J. Hematol.* (1980) 25, pp. 134–140.
Little and Rumsby, "Lysis of Erythrocytes from Stored Blood by Phospholipase C", *Bio Chemical Journal*, (1980), vol. 188, pp. 39–46.
Laczko et al., "Discocyte, Echinocyte Reversibility and Blood Stored in CPD Over a Period of 56 Days", *Transfusion*, Jul.–Aug. 1979, pp. 379–388.
Fischer-Chem. Abst. vol. 59 (1963) p. 3170G.

*Primary Examiner*—Sam Rosen
*Attorney, Agent, or Firm*—Paul C. Flattery; Daniel D. Ryan

[57] ABSTRACT

An additive solution is used to preserve normal red blood cell morphology during storage. The solution comprises a concentration of a nontoxic, physiologically compatible sterol, such as cholesterol, epi-cholesterol, lanosterol, stigmasterol, ergosterol, desmosterol, fucosterol, cholestanol, epi-cholestanol, coprosterol, epi-coprosterol, lathosterol, or campesterol. The sterol is present in a concentration of between approximately 1.0 and 3.0 milligrams per milliliter of whole blood.

18 Claims, 2 Drawing Figures

ADDITIVE STEROL SOLUTION AND METHOD FOR PRESERVING NORMAL RED CELL MORPHOLOGY IN WHOLE BLOOD DURING STORAGE

TECHNICAL FIELD OF THE INVENTION

The invention generally relates to methods and materials associated with the storage of whole blood.

DESCRIPTION OF THE PRIOR ART

Whole blood may be collected and stored in the presence of an anticoagulant under conventionally specified conditions for approximately 28 days prior to administration to a patient.

The amount of hemoglobin present in stored blood is known to increase during storage, because, during storage, red blood cells rupture. This phenomenon is generally referred to as hemolysis. It is desirable, of course, to prevent or minimize hemolysis during storage.

In Buckles et al U.S. Pat. No. 4,326,025, the use of emulsions of certain ester materials is disclosed to prevent hemolysis in stored blood. As discussed in the Buckles et al application, the presence of diester materials, such as di-2-ethylhexylphthalate (hereafter called DEHP), or tri-2-ethylhexylphosphate, in stored blood in concentrations of 50 to 100 parts per million is observed to supress hemolysis.

Similarly, in Smith U.S. Pat. No. 4,222,379, and also in Geissler et al. U.S. patent application Ser. No. 105,469 filed Dec. 19, 1979, blood bags plasticized with a diester material, such as DEHP, are observed to reduce the hemolysis of blood therein stored. The DEHP leaches gradually from the walls of the blood bag into the blood and provides a final concentration of DEHP after 21 days of storage of about 30 to 100 micrograms per milliliter of blood.

In addition to hemolysis, it has also been observed that, during storage, red blood cells undergo morphological changes. After even only a few days of storage, a large percentage of the red blood cells lose their normal disc-shaped appearance and develop spicules or crenations. After longer periods of storage, these crenated red cells further assume a generally spherical shape.

It is commonly believed that crenated red cells are capable of regaining their normal disc-shape and organic functions after reinfusion. However, if the red cells have developed the generally spherical shape, it is commonly believed that the red cells have been irreversibly damaged and cannot again regain their normal shape and functions after reinfusion.

Concentrations of the antihemolytic agents on the order disclosed in the above-discussed Buckles et al application and the Smith Patent do not have a significant effect in reducing morphological changes in the red cells during storage. For example, after exposure to a concentration of as much as 100 micrograms of DEHP per milliliter of whole blood, more than 75 percent of the red cells may still exhibit a crenated morphology after seven days of storage.

In this regard, attention is directed to Estep U.S. Pat. No. 4,386,069, entitled AN ADDITIVE SOLUTION AND METHOD FOR PRESERVING NORMAL RED CELL MORPHOLOGY IN WHILE BLOOD DURING STORAGE, which shares the same filing date and assignee as this application. As disclosed in this copending application, the addition of a fatty ester, such as DEHP, in concentrations of between 150 and 3,000 micrograms per milliliter of whole blood has been observed to significantly enhance the preservation of normal red cell morphology in whole blood during storage.

Another discussion of the morphological changes which red blood cells undergo during storage is found in the article by Little and Rumsby, *Scand. J. Haematol.* (1980) 25, pages 134-140. The article observes that storage of blood in glass bottles accelerates both morphological change and susceptibility of hemolysis, when compared with the normal plastic transfusion packs. A related article by the same authors is found in the *Biochemical Journal* (1980), Volume 188, pages 39-46.

In the book by Eric Ponder entitled *Hemolysis and Related Phenomena*, Grune and Stratton, New York (1948), at pages 263-287, it is noted that there is a correlation between plasma cholesterol levels and the inhibition of the lysing of blood cells stored for 25 hours at 37° C., the lysing being deliberately caused by the addition of saponin or related lysins. This relatively short-term induced lysing of the red blood cells is believed to be an entirely different mechanism from the long-term hemolysis previously referred to, which is encountered in blood stored at substantially lower temperatures (approximately 4° C.) for substantially longer periods of time (for example, 21 or 35 days) in the presence of a known anticoagulant and to which no saponin or other lysins are added.

In an article by Richard A. Cooper et al. entitled "Modification of Red Cell Membrane Structure by Cholesterol-Rich Lipid Dispersions", *Journal of Clinical Investigation*, Volume 55 (1975), pages 115-126, the effect of cholesterol on cell shape is described. Cholesterol-poor red cells are stated to be spherocytic in appearance, while cholesterol-rich cells are broad and flat. Also, cholesterol-poor cells are stated to have increased osmotic fragility. However, this is not seen to be a direct cause of hemolysis in blood stored for a period of days, because the red cells in stored blood are not believed to be under significant osmotic stress.

Finally, the article by DeVenuto et al. entitled *Distribution of Progresterone and its Effect on Human Blood During Storage*, found in *Transfusion*, Volume 16 (1976), pages 107-112 observes that progesterone improves the resistance of cells to lysis on storage for 42 days.

It is fair to state that the chemistry and function of the morphological changes of red blood cells and their hemolysis during long-term storage is not well understood.

It is one of the principal objects of this invention to provide a means for preserving red morphology in whole blood during storage.

SUMMARY OF THE INVENTION

To achieve this and other objects, the invention provides an additive solution which can be introduced into whole blood to enhance the preservation of normal red cell morphology during storage. The solution comprises a physiologically blood compatible sterol which is introduced into the whole blood in an amount to provide, after its introduction, a concentration of the sterol of between approximately 1.0 and 3.0 milligrams per milliliter of whole blood.

In order to maximize the morphological effect of the solution, the solution preferably includes the sterol in a concentration of generally between approximately 2.0 and 3.0 milligrams per milliliter of whole blood. At these higher concentrations, the solution is observed to lead to a twenty-five fold increase in the number of normal red cells after thirty-five days of storage.

In all of the preferred embodiments, the sterol is cholesterol which is introduced into the whole blood in the form of an emulsion.

The additive solution which embodies the features of the invention is preferably introduced into the whole blood at the outset of the storage period, regardless of the beneficial effect or effects desired.

The invention also provides a method for storing whole blood, which method comprises introducing the above-described solutions into the whole blood.

Other features and advantages of the embodiments of the invention will become apparent upon reviewing the following more detailed description and Examples, the drawings, and the appended claims.

Before explaining the embodiments of the invention in detail, it is to be understood that the invention is not limited in its application to the details as set forth in the following description, Examples, or as illustrated in the accompanying drawings. The invention is capable of other embodiments and of being practiced or carried out in various ways. Furthermore, it is to be understood that the phraseology and terminology employed herein is for the purpose of description and should not be regarded as limiting.

DESCRIPTION OF THE PREFERRED EMBODIMENT

Figure 1:
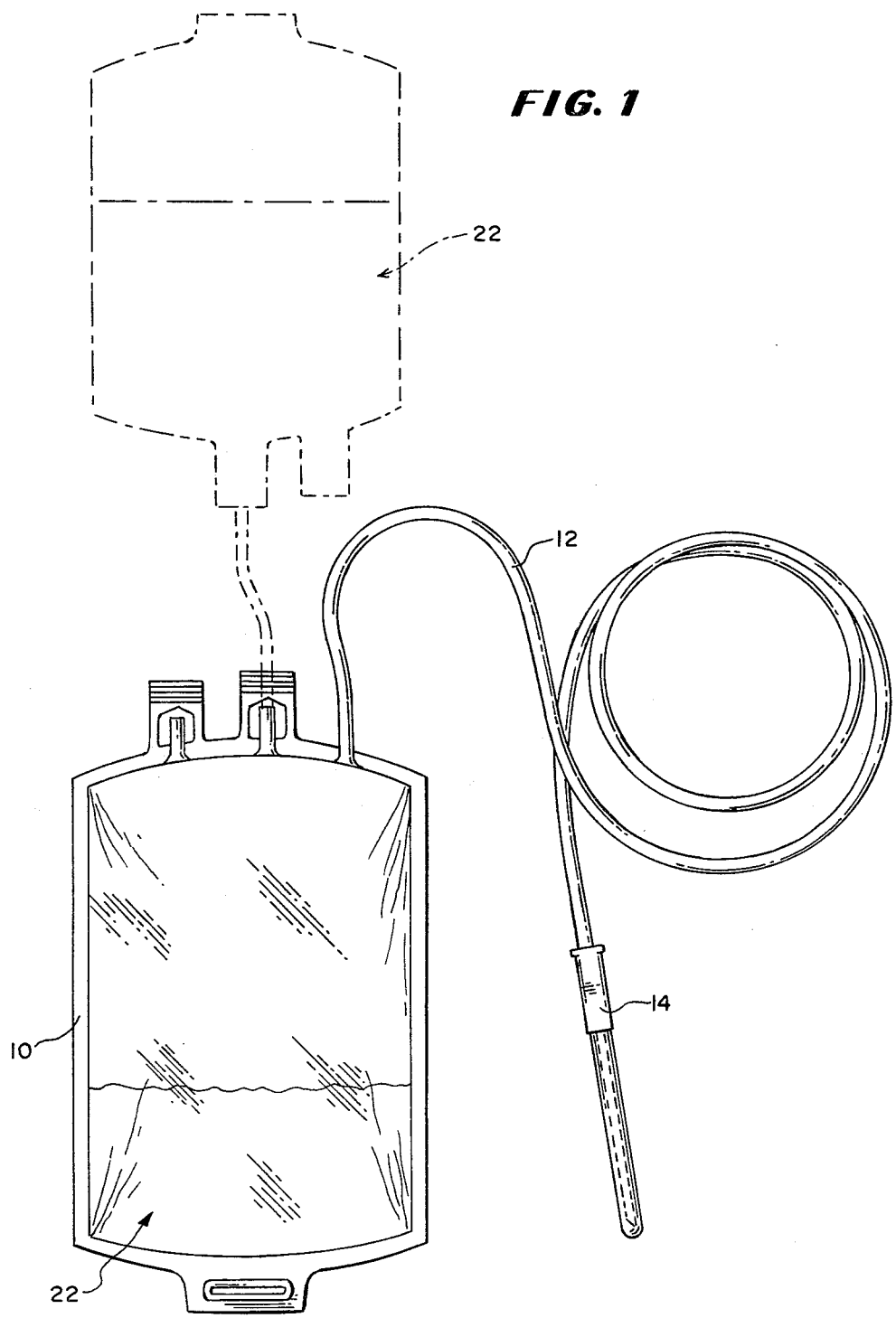
FIG. 1 is a plan view of a blood bag containing a solution which embodies various of the features of the invention.

A blood collection and storage container 10 is shown in FIG. 1. The container 10 is typically made from medical grade polyvinyl chloride plastic. The container 10 includes a donor tube 12 and a phlebotomy needle 14, through which whole blood from a patient or donor is introduced into the container 10 for storage. An anticoagulant solution is carried within the container 10 to prevent the collected whole blood from clotting during the collection procedure and subsequent storage.

Typically, during storage, the whole blood is subjected to a temperature of about 4° C. The storage period typically lasts between 21 and 35 days.

During storage, a percentage of the red blood cells are known to lyse, or rupture, and release hemoglobin into the plasma. In addition, within the first few days of storage, a great number of red blood cells are observed to undergo an undesirable morphological transition from a normal biconcave disc-shape (shown by the normal red cells 16, or erythrocytes, in FIG. 2) to form spicules or crenations (shown by the crenated red cells 18, or echinocytes, in FIG. 2). By the seventh day of storage, the great majority of the red blood cells (more than 75 percent) will have undergone this undesirable morphological change and display marked spiculation.

Figure 2:
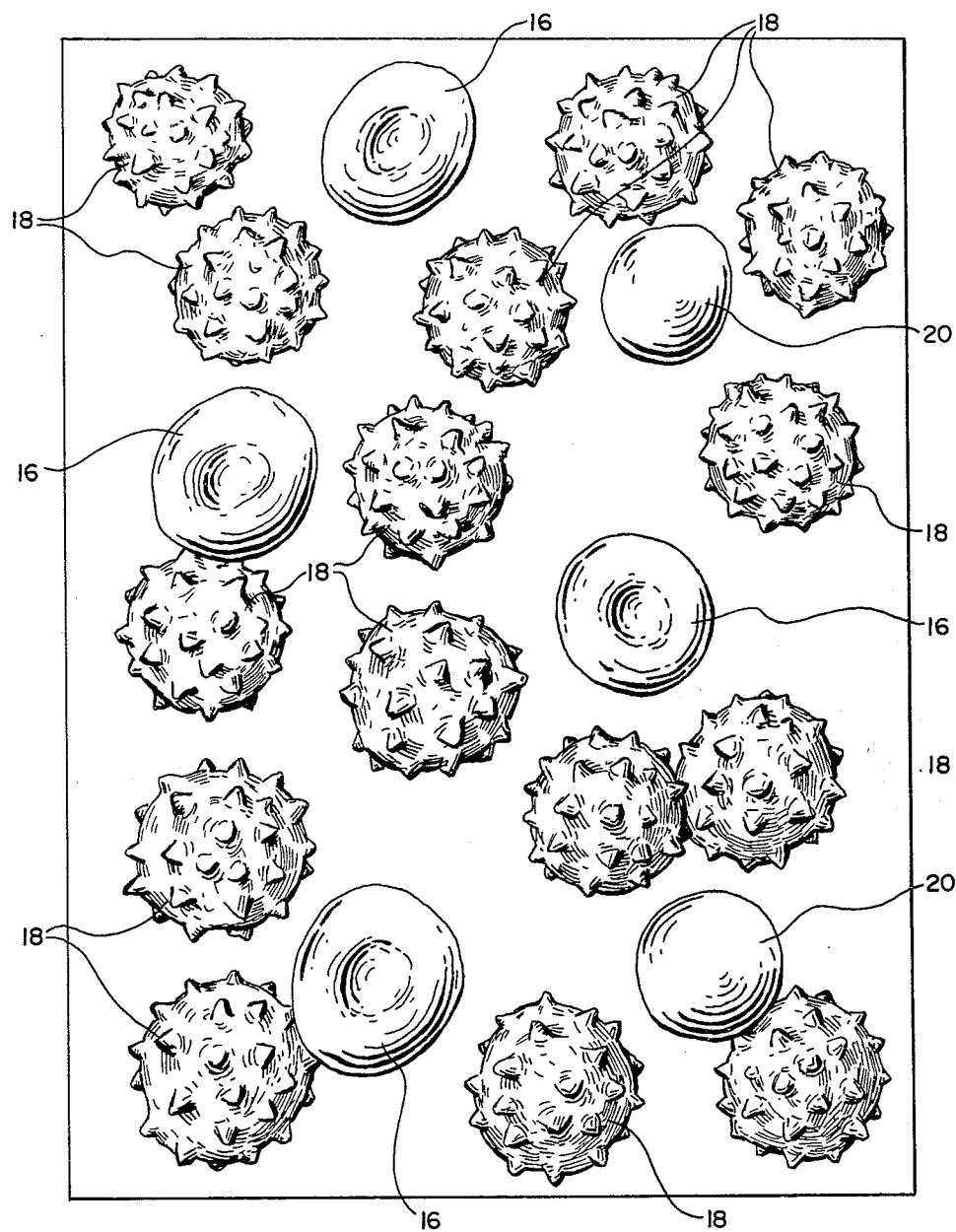
FIG. 2 is a generally pictorial, microscopic plan view of a stored whole blood sample which includes both normal red cells and red cells which have undergone morphological changes.

During further storage, the crenated red cells 18 further evolve into spiculate spheres (shown by the spherical red cells 20, or sphereochinocytes, in FIG. 2). This morphology is thought to indicate irreversible cell damage and an inability of the red cells so effected to regain their natural functions upon reinfusion.

These undesired morphological changes in the red cells take place even when the whole blood is stored in conventional polyvinyl chloride blood containers plasticized with DEHP, which is known to leach into the whole blood and suppress red cell hemolysis during storage.

To reduce red blood cell hemolysis and/or to preserve red blood cell morphology during the storage period, the invention provides an additive solution 22 which can be introduced into the whole blood stored in the container 10. The additive solution 22 includes a physiologically blood compatible sterol which is introduced into the whole blood in an amount to provide, after its introduction, a concentration of between approximately 0.05 and 3.0 milligrams of the sterol per milliliter of whole blood.

The sterol is preferably cholesterol, although it is believed that other sterols which are nontoxic and physiologically compatible with whole blood in the above range of concentrations can be utilized. Such alternative sterols include epi-cholesterol, lanosterol, stigmasterol, ergosterol, desmosterol, fucosterol, cholestanol, epi-cholestanol, coprosterol, epi-coprosterol, lathosterol and campesterol.

Preferably, the sterol solution 22 is uniformly dispersed into the whole blood in the form of an emulsion. The emulsion may contain any of the above-described sterols emulsified with a sufficient quantity of a hemocompatible surfactant to stabilize the emulsion for a period of time which is at least equal to the time the emulsion is exposed to the blood. Of course, indefinitely stable emulsions are preferred.

Such indefinitely stable emulsions are preferably made by first mixing the sterol material with a hemocompatible surfactant or emulsifying agent in the substantial absence of water. After intimate mixing of the sterol with the agent, the mixture is added to the water ingredient to form the emulsion.

Any blood-compatible, non-toxic surfactant or emulsifying agent may be used for forming the emulsion, such as polysorbate 80 (as identified in the U.S. Pharmacopoea), which is a mixture of polyoxyethylene ethers of mono oleic ester of sorbitan and sold, for example, as Tween 80 by ICI Americas, Inc. Polyoxyethylene (20) sorbitan monopalmitate can also be used, which is sold by the same company as Tween 40. Other examples of possible emulsifiers include sodium deoxycholate and poloxamers 108, 188, 338, and 407 (as defined by the Cosmetics, Toiletry and Fragrance Association). These poloxamers are poly(oxypropylene) poly-(oxyethylene) copolymers and are sold, for example, as Pluronic F-38, F-108, and F-127 Polyols, respectively, by the BASF Wyandotte Corporation.

It has been observed that certain emulsifiers, which have a relatively high affinity for cholesterol or other sterol utilized, such as egg phosphatidycholine, are less preferred for use in association with the solution 22. It is believed that, due to the high affinity between these emulsifiers and the sterol, the sterol is partially sequestered and unavailable for its maximum desired effect in accordance with this invention.

The solution 22 is preferably introduced into the whole blood at the outset of the storage period. The solution 22, thus, can constitute a red blood cell storage solution carried in the container 10 prior to venipuncture.

In this embodiment, the storage solution 22 would preferably include, as a part thereof, an anticoagulant solution, such as heperin, citrate, or ethylene diamine tetraacetic acid. The storage solution 22 may also include a nutrient added to the anticoagulant, such as phosphate or dextrose, with or without adenine.

Alternatively, and as is shown in phantom lines in FIG. 1, the storage solution 22 may be added to the whole blood/anticoagulant solution carried in the container 14.

As the following Examples I, II, and III demonstrate, the sterol solution 22 sufficient to provide, after its introduction into the whole blood, a concentration of between 0.05 milligram and 2.0 milligrams of the sterol per milliliter of whole blood serves to effectively surpress the spontaneous hemolysis of red cells during storage. The most effective suppression of hemolysis occurs when the concentration of the sterol is between approximately 0.1 milligram and 0.8 milligram per milliliter of whole blood. At these preferred concentrations, plasma hemoglobin levels are reduced by nearly one-third. Concentrations of the sterol above and below this optimal range have not been observed to suppress hemolysis as well as concentrations within the optimal range.

As the following Example IV demonstrates, in addition to suppressing red cell hemolysis during storage, whole blood into which the solution 22 has been introduced at the outset of storage displays substantially lower percentages of crenated red cells throughout the storage period than whole blood into which no solution 22 was added. After thirty-five days of storage, percentages of normal red cells are, on the average, up to twenty-five times higher in whole blood exposed to the sterol solution 22 than in whole blood not so exposed.

However, it has been discovered that the effect of the solution 22 in suppressing red cell hemolysis is not directly related to the effect of the solution 22 in suppressing morphological changes. The morphological transition of the stored red blood cells into the crenated form occurs generally more quickly than the hemolysis of the red cells. Indeed, a majority of the red cells often assume their crenated form after just seven days of storage, whereas, after seven days of storage, the plasma hemoglobin of unprotected blood is still normally relatively low.

It has thus been determined that the concentrations of the sterol which most effectively suppresses morphological changes in the red cells differs somewhat from the above-described concentrations associated with the reduction of red cell hemolysis. More particularly, higher concentrations of the sterol in excess of approximately 0.4 milligram per milliliter of whole blood, and preferably between approximately 2.0 and 3.0 milligrams per milliliter of whole blood, are desirable in order to achieve the optimal benefit of the sterol in suppressing the evolution of red cells during storage into the abnormal, crenated form.

In order to achieve a substantial amount of both desirable effects, it is preferable for the sterol to be present in the whole blood in a concentration of between apprixi-mately 0.4 and 2.0 milligrams per milliliter of whole blood. In this range of concentrations, a substantial amount of both desirable effects is observed, i.e., the suppression of spontaneous hemolysis, as well as the suppression of changes of cell morphology during the storage.

If, however, it is desired only to maximize the effect of suppression of the change in red cell morphology, the concentration of the sterol may be raised to the levels heretofore described. On the other hand, if one wishes only to maximize suppression of hemolysis on storage, the concentration of the sterol may be lowered to the levels heretofore described.

The marked reduction of red cells undergoing hemolysis and, in particular, morphological changes strongly suggests that red blood cells stored in the presence of the solution 22 exhibit an enhanced posttransfusion survival rate.

The following examples are for illustrative purposes and are not intended to limit the invention described herein. It should also be understood that the specific quantitative results obtained in each Example (e.g., the absolute amount of plasma hemoglobin, or the absolute number of normal red cells as compared with the absolute number of crenated or spherical red cells) can and do vary according to the blood physiology of the individual donor involved.

EXAMPLE I

Cholesterol was emulsified with an equal weight of Tween 80 to provide one cholesterol formulation, while another batch of cholesterol was mixed with an equal weight of egg phosphatidylcholine (E.P.C.). Both of these mixtures were separately suspended in 0.154 M. sodium phosphate buffer at pH 7.4, and further dispersed by sonication (ultrasonic dispersion) in a bath-type sonifier.

A stock emulsion was prepared containing 12 milligrams of E.P.C. and 6 milligrams of cholesterol per milliliter of solution. Another stock emulsion was prepared containing equal concentrations of 6 milligrams of cholesterol and Tween 80 per milliliter of solution.

One milliliter of each of these stock emulsions was added to separate 10 ml. aliquots of blood stored in sterile polypropylene tubes. These aliquots were drawn from blood stored in a blood bag made of a hemocompatible plastic free of phthalate-type plasticizers and containing CPD anticoagulant.

The nominal concentration of added cholesterol was 0.55 milligrams per milliliter of whole blood.

A buffer control sample was also prepared by adding one milliliter of the phosphate buffer to a 10 milliliter aliquot of blood.

The blood samples were stored in the sterile polypropylene tubes at 4° C. for 28 days. Each sample was assayed for plasma hemoglobin content (mg%) at weekly intervals, utilizing a chemical assay using tetramethylbenzidine. The results are shown in Table I below and are expressed as the average of triplicate determinations, plus or minus one standard deviation.

TABLE 1

| Sample | Plasma Hemoglobin Concentration (mg %) on the Days of Storage Indicated Below | | | | |
|---|---|---|---|---|---|
| | 1 | 7 | 14 | 21 | 28 |
| Buffer Control | 4.3 ± 0.1 | 7.0 ± 0.2 | 19.6 ± 0.1 | 66.0 ± 2.4 | 122.6 ± 1.3 |
| Cholesterol Suspended With Egg Phosphatidylcholine* | 3.7 ± 0.2 | 4.3 ± 3.5 | 20.9 ± 0.1 | 55.1 ± 2.9 | 110.2 ± 0.2 |

TABLE 1-continued

| | Plasma Hemoglobin Concentration (mg %) on the Days of Storage Indicated Below | | | | |
|---|---|---|---|---|---|
| Sample | 1 | 7 | 14 | 21 | 28 |
| Cholesterol Suspended With Tween 80* | 4.7 ± 0.1 | 7.1 ± 0.2 | 10.9 ± 0.1 | 29.3 ± 0.8 | 47.6 ± 0.6 |

*NOTE: Nominal concentration of .55 milligrams of cholesterol per milliliter of whole blood Table 1 clearly demonstrates that, beginning with the fourteenth day of storage, cholesterol (especially when suspended or emulsified in Tween 80) provides a significant suppression in the development of plasma hemoglobin in the whole blood, when compared with whole blood stored only in contact with the buffer control. By the twenty-eighth day of storage, plasma hemoglobin concentrations of whole blood stored in the presence of the cholesterol/Tween 80 solution were nearly one-third the hemoglobin concentrations of whole blood stored in the presence of the buffer control.

EXAMPLE II

A stock emulsion was prepared containing 440 milligrams of cholesterol and an equal weight of Tween 80 in 10 milliliters of isotonic sodium phosphate buffer of pH 7.4. The Tween 80-cholesterol mixture was suspended by vortex agitation for 3 minutes and dispersed by sonication in a bath-type sonifier for one hour. A series of dispersions of lower cholesterol content were than prepared by diluting 2.0, 1.0, 0.5, 0.25, and 0.1 milliliters of the stock emulsion with additional phosphate buffer to form separate 4.0 milliliter solutions.

Blood was obtained from six different donors by drawing into plastic syringes containing CPD anticoagulant. Seven aliquots, each containing three milliliters of whole blood, were taken from each syringe and added to sterile polypropylene tubes. To each tube from a given donor was added 0.3 milliliter of a different cholesterol dispersion, or in the case of the control, pure phosphate buffer. All tubes were then capped; the contents mixed by inversion; and the samples stored at 4° C. for 35 days.

After 21 days, the plasma hemoglobin concentration (mg%) in the blood was determined as described in Example I. The plasma hemoglobin concentrations are as indicated in Table 2 below. the average results are expressed as the average of six samples plus or minus one standard deviation, except for the 0.38 milligram of cholesterol per milliliter concentration, for which five samples were analyzed.

TABLE 2

| | Plasma Hemoglobin Concentration (mg %) After 21 Days of Storage | | | | | | |
|---|---|---|---|---|---|---|---|
| Concentration of Cholesterol Added Per Milliliter of Whole Blood | Blood Sample | | | | | | |
| | A | B | C | D | E | F | Average |
| 0 mg./ml. | 56.6 | 86.8 | 48.8 | 38.8 | 100.3 | 32.1 | 60.6 ± 27.2 |
| 0.075 mg./ml. | 22.6 | 26.2 | 48.0 | 38.9 | 16.4 | 21.6 | 29.0 ± 12.0 |
| 0.19 mg./ml. | 25.1 | 16.1 | 34.8 | 30.2 | 34.9 | 18.9 | 26.7 ± 8.0 |
| 0.38 mg./ml. | 31.7 | 33.7 | 22.5 | 21.6 | 13.5 | — | 24.6 ± 8.2 |
| 1.14 mg./ml. | 22.1 | 51.7 | 42.7 | 45.6 | 29.2 | 18.5 | 35.0 ± 13.6 |
| 1.45 mg./ml. | 34.8 | 46.2 | 29.1 | 88.2 | 26.4 | 14.7 | 39.9 ± 25.8 |
| 3.00 mg./ml. | 66.9 | 149.8 | 52.6 | 80.8 | 92.4 | 36.7 | 79.9 ± 39.6 |

Table 2 clearly demonstrates that the lowest plasma hemoglobin concentrations were obtained at cholesterol concentrations on the order of 0.075, 0.19, and 0.38 milligrams per milliliter. At higher and lower concentrations of cholesterol the plasma hemoglobin content was higher.

It can also be seen that the plasma hemoglobin concentration of stored blood from different donors can vary widely. Nevertheless, in all instances the relative plasma hemoglobin concentration can be suppressed by a proper concentration of the dispersed cholesterol.

EXAMPLE III

The experiment of Example III was continued, with the plasma hemoglobin concentration (mg%) of the various blood samples being determined after 35 days of storage. The results are indicated in Table 3 below.

TABLE 3

| | Plasma Hemoglobin Concentration (mg %) After 35 Days of Storage | | | | | | |
|---|---|---|---|---|---|---|---|
| Concentration of Cholesterol Added | Blood Sample | | | | | | |
| | A | B | C | D | E | F | Average |
| 0 mg./ml. | 295.3 | 299.2 | 149.0 | 176.9 | 290.0 | 89.6 | 216.7 ± 90.2 |
| 0.075 mg./ml. | 96.9 | 76.3 | 86.3 | 82.0 | 66.3 | 159.2 | 94.5 ± 33.3 |
| 0.19 mg./ml. | 125.7 | 41.2 | 65.7 | 59.7 | 70.8 | 81.9 | 74.2 ± 28.6 |
| 0.38 mg./ml. | 86.0 | 149.0 | 53.6 | 42.8 | 36.2 | — | 73.5 ± 46.3 |
| 1.14 mg./ml. | 69.3 | 239.8 | 111.2 | 124.1 | 118.8 | 94.4 | 126.3 ± 59.1 |
| 1.45 mg./ml. | 160.7 | 214.3 | 82.6 | 153.0 | 128.9 | 98.7 | 139.7 ± 47.4 |
| 3.00 mg./ml. | 265.2 | 467.4 | 173.5 | 182.1 | 214.3 | 123.4 | 237.7 ± 121.9 |

Table 3 demonstrates that, after 35 days of storage, the lowest plasma hemoglobin concentrations are still generally at the cholesterol concentrations encountered in Example II.

EXAMPLE IV

The experiment of Examples II and III was continued, with blood from each of the sample being examined by light microscopy after 35 days of storage to determine the percentage of red blood cells having normal morphology, when compared with blood cells having spiculated or spherical morphologies. The percentages of red blood cells of normal morphology found in the samples is shown below in Table 4.

TABLE 4

| Percentage of Red Blood Cells of Normal Morphology in Whole Blood Stored at 4° C. for 35 Days With Varying Concentrations of Cholesterol Emulsified with Tween 80 | | | | | | | |
|---|---|---|---|---|---|---|---|
| Concentration of Cholesterol Added | Blood Sample | | | | | | |
| | A | B | C | D | E | F | Average |
| 0 mg./ml. | 0.6 | 3.9 | 2.5 | 2.0 | 0.8 | 2.8 | 2.1 ± 1.3 |
| 0.075 mg./ml. | 3.8 | 1.8 | 7.4 | 5.8 | 8.9 | 12.5 | 6.7 ± 3.8 |
| 0.19 mg./ml. | 4.4 | 6.1 | 8.6 | 7.2 | 4.5 | 15.3 | 7.7 ± 4.1 |

TABLE 4-continued

Percentage of Red Blood Cells of Normal Morphology in Whole Blood Stored at 4° C. for 35 Days With Varying Concentrations of Cholesterol Emulsified with Tween 80

| Concentration of Cholesterol Added | Blood Sample | | | | | | |
|---|---|---|---|---|---|---|---|
| | A | B | C | D | E | F | Average |
| 0.38 mg./ml. | 4.9 | 11.5 | 14.6 | 10.8 | 13.1 | — | 11.0 ± 3.7 |
| 1.45 mg./ml. | 20.4 | 33.2 | 28.5 | 26.6 | 68.6 | 42.0 | 36.6 ± 17.3 |
| 3.00 mg./ml. | 32.2 | 55.8 | 48.4 | 33.5 | 46.9 | 56.7 | 45.6 ± 10.6 |

It can be seen that increasing quantities of cholesterol result in significantly increased percentages of blood cells having normal morphology after 35 days of storage. The optimum dosage of cholesterol in terms of preserving the morphology of the blood cells appears to be at 3 milligrams per milliliter, or higher.

However, as can be observed from the data in Examples II and III, such higher concentrations do not tend to suppress plasma hemoglobin concentrations. Thus, it is thought preferably to use less than 3.0 milligrams of cholesterol per milliliter of whole blood, so that a significant suppression of hemolysis can also be obtained along with a reduction in the cells of abnormal morphology.

Various of the features of the invention are set forth in the following claims.

I claim:

1. An additive solution for preserving normal red blood cell morphology during whole blood storage, said solution comprising
    a physiologically blood compatible sterol present in a concentration of between approximately 1.0 and 3.0 milligrams per milliliter of whole blood.

2. An additive solution according to claim 1 wherein said sterol is cholesterol.

3. An additive solution according to claim 1 wherein said sterol is in the form of an emulsion.

4. An additive solution according to claim 1 and further including, as part of said solution, an anticoagulant.

5. An additive solution according to claim 4 and further including, as part of said solution, a nutrient for the whole blood.

6. An additive solution according to claim 1 wherein said sterol is present in a concentration of between approximately 2.0 and 3.0 milligrams per milliliter of whole blood.

7. A whole blood storage system comprising
    a container having an interior for receiving whole blood for storage,
    a solution carried within said interior and including a physiologically blood compatible sterol present in a concentration of between approximately 1.0 and 3.0 milligrams per milliliter of whole blood stored within said container.

8. A whole blood storage system according to claim 7 wherein said sterol is present in a concentration of between approximately 2.0 and 3.0 milligrams per milliliter of whole blood.

9. A whole blood storage system according to claim 7 or 8 wherein said sterol is cholesterol.

10. A whole blood storage system according to claim 7 or 8 wherein said sterol is in the form of an emulsion.

11. A whole blood storage system according to claim 7 or 8 wherein said solution further includes, as a part thereof, an anticoagulant.

12. A whole blood storage system according to claim 11 wherein said solution further includes, as a part thereof, a nutrient for the whole blood.

13. A whole blood storage system according to claim 12 wherein said container includes
    a donor tube having an end attached in flow communication with said interior and an opposite end, and
    a phlebotomy needle attached in flow communication with said opposite end.

14. A method for storing whole blood so as to preserve normal red blood cell morphology during the storage period, said method comprising the step of
    introducing for each milliliter of whole blood present between approximately 1.0 and 3.0 milligrams of a physiologically blood compatible sterol.

15. A method according to claim 14 and further including, prior to said sterol introduction step, the step of emulsifying the sterol.

16. A method according to claim 14 wherein said sterol introduction step includes introducing the sterol at the outset of the storage period.

17. A method according to claim 14 wherein the sterol utilized is cholesterol.

18. A method according to claim 14 wherein said sterol introduction step includes the step of introducing, for each milliliter of whole blood, between approximately 2.0 and 3.0 milligrams of a physiologically blood compatible sterol.

* * * * *